(12) United States Patent
Soun et al.

(10) Patent No.: US 7,029,494 B2
(45) Date of Patent: Apr. 18, 2006

(54) BRAIDED MODULAR STENT WITH HOURGLASS-SHAPED INTERFACES

(75) Inventors: Naroun Soun, Lawrence, MA (US); Kimberly Un, Lexington, MA (US); Robert C. Thistle, Brockton, MA (US); Raymond J. Laliberte, Chepachet, RI (US)

(73) Assignee: Scimed Life Systems, Inc., Maple Grove, MN (US)

( * ) Notice: Subject to any disclaimer, the term of this patent is extended or adjusted under 35 U.S.C. 154(b) by 498 days.

(21) Appl. No.: 10/072,567

(22) Filed: Feb. 8, 2002

(65) Prior Publication Data

US 2003/0153973 A1 Aug. 14, 2003

(51) Int. Cl.
 *A61F 2/06* (2006.01)
(52) U.S. Cl. .................................... 623/1.15
(58) Field of Classification Search ...... 623/1.11–1.22; 606/108, 194, 195; 608/198
 See application file for complete search history.

(56) References Cited

U.S. PATENT DOCUMENTS

| 4,655,771 A | 4/1987 | Wallsten |
| 5,064,435 A | 11/1991 | Porter |
| 5,540,704 A | 7/1996 | Gordon et al. |
| 5,575,818 A | 11/1996 | Pinchuk |
| 5,665,117 A | 9/1997 | Rhodes |
| 5,693,088 A | 12/1997 | Lazarus |
| 5,709,713 A | 1/1998 | Evans et al. |
| 5,725,547 A | 3/1998 | Chuter |
| 5,843,160 A | 12/1998 | Rhodes |
| 5,993,483 A | 11/1999 | Gianotti |
| 6,015,431 A | 1/2000 | Thornton et al. |
| 6,293,969 B1 * | 9/2001 | Chuter ...................... 623/1.16 |
| 6,325,822 B1 | 12/2001 | Chouinard et al. |
| 6,398,807 B1 | 6/2002 | Chouinard et al. |
| 6,610,087 B1 * | 8/2003 | Zarbatany et al. ......... 623/1.32 |
| 6,648,913 B1 * | 11/2003 | Yee et al. .................. 623/1.35 |
| 2001/0044647 A1 | 11/2001 | Pinchuk et al. |
| 2002/0007210 A1 | 1/2002 | Chouinard et al. |

FOREIGN PATENT DOCUMENTS

| EP | 0 183 372 A1 | 6/1986 |
| EP | 0 775 471 A1 | 5/1997 |
| EP | 0 880 948 A1 | 12/1998 |

(Continued)

OTHER PUBLICATIONS

U.S. Appl. No. 09/442,192, filed as Nov. 16, 1999, "Endoluminal Stent Having a Matched Stiffness Region and/or a Stiffness Gradient and Methods for Providing Stent Kink Resistance", Zarbatany et al. (BSI-410).

(Continued)

*Primary Examiner*—Vy Bui
(74) *Attorney, Agent, or Firm*—RatnerPrestia (57) ABSTRACT

A braided modular stent comprising a first component and a second component, each component comprising an hourglass-shaped interface having a reduced diameter section positioned between two sloped sections. Each sloped section extends between the reduced diameter section and one of a plurality of nominal diameter sections. The reduced diameter section has a greater radial strength than the nominal diameter sections. One of the components may have a sealing region, such as a circumferential elevation, for providing an endoleak-resistant seal between the stent and a body lumen. One exemplary method for fabricating a circumferential elevation comprises affixing a plurality of filaments, such as sutures, between overlaps of braided filaments in one region and overlaps in another region.

33 Claims, 4 Drawing Sheets

FOREIGN PATENT DOCUMENTS

| | | |
|---|---|---|
| WO | WO 00/74598 A1 | 12/2000 |
| WO | WO 01/35864 A1 | 5/2001 |

OTHER PUBLICATIONS

U.S. Appl. No. 09,442,165; filed Nov. 16, 1999, "Multi-section Filamentary Endoluminal Stent", Chouinard et al. (BSI-400).

U.S. Appl. No. 09/327,069, filed Jun. 7, 1999, Improved-Guidewire-Access Modular Intraluminal Prosthesis with Connecting Selection, Yee et al. (BSI-280).

Invitation to Pay Additional Fees w/ Communication relating to the Results of the Partial International Search, dated Aug. 1, 2003, in corresponding PCT patent application PCT/US03/02721.

* cited by examiner

BRAIDED MODULAR STENT WITH HOURGLASS-SHAPED INTERFACES

BACKGROUND OF THE INVENTION

1. Technical Field

This invention relates generally to endoluminal devices and, more specifically, to a stent having an integral sealing ring.

2. Background of the Invention

A stent is an elongated device used to support an intraluminal wall. Stents may also have a prosthetic graft layer of fabric or covering lining the inside or outside thereof, such a covered stent being commonly referred to in the art as an intraluminal prosthesis, an endoluminal or endovascular graft (EVG), or a stent-graft. A prosthesis may be used, for example, to treat a vascular aneurysm by removing the pressure on a weakened part of an artery so as to reduce the risk of rupture. Stents and prostheses are typically introduced into a lumen in a compressed state and expanded to an expanded state by self-expansion, balloon-expansion, or a combination thereof.

Various stent architectures are known in the art, including filamentary and cut tube architectures. Braided and wound architectures are subclasses of architectures within the filamentary class of architectures. Included among the braided filamentary stent architectures are those described in U.S. Pat. No. 4,655,771 to Hans I. Wallsten and incorporated herein by reference. The '771 Wallsten patent is only one example of many variations of braided stents known in the art, however, and thus not intended as a limitation of the invention described herein later. Braided stents tend to be very flexible, having the ability to be placed in tortuous anatomy and still maintain patency. This flexibility of braided stents make them particularly well-suited for treating aneurysms in the aorta, where often the lumen of the vessel becomes contorted and irregular both before and after placement of the stent.

As used herein, flexibility or stiffness can be described in terms of the amount of force required to bend a stent into an arc. The force required to bend a tubular stent of a particular length into a given arc having a central angle and a given arc radius, is a measure of the stent flexibility. Thus, comparing two stents of equal length with different stent architectures, the stent requiring greater force to bend it into a given arc is relatively stiffer, whereas the stent requiring lesser force is relatively more flexible. It is not uncommon for a stent to be installed in a lumen that is somewhat tortuous in nature. In such cases, there is a need for the prosthesis to be flexible or bendable without kinking, especially in the region where the stent is inflected in its deployed configuration.

One disadvantage of braided stents is typically that the radial strength on the end of the braided stent may be substantially less than the radial strength in the middle of the stent. As used herein, "radial strength" can be described generally as the resistance of a stent to radial compression. A stent with more radial strength exerts a greater outward radial force when compressed than does a stent with less radial strength. Insufficient radial strength on the stent ends may result in an incomplete seal or migration of the device after implantation.

An incomplete seal between the outer wall of the prosthesis and the inner wall of the lumen may allow intraluminal fluid to leak between the prosthesis and the lumen wall. Similarly, an incomplete seal between the outer wall of a first modular stent component and the inner wall of a second modular stent component may allow intraluminal fluid to leak between the mating modular components or relative movement of the two stent components. Such leaks, sometimes referred to as an "endoleaks," may cause a number of problems including fatality, for patients experiencing such leaks. Thus, it is desirable to provide a prosthesis that minimizes the potential for endoleaks.

Various designs have been proposed to minimize endoleaks. For example, U.S. patent application Ser. No. 09/327,069, filed Jun. 7, 1999, by Staudenmeier et al. assigned to the assignee of this invention, and incorporated herein by reference, describes one modular stent embodiment wherein interfacing components have interlocking, hourglass-shaped ends to provide a fluid-tight seal. The teachings of this application, however, are not specific to any particular type of stent architecture. U.S. patent application Ser. No. 09/442,165, filed Nov. 16, 1999, by Chouinard et al., also assigned to the assignee of this invention and incorporated herein by reference, discloses overcoming typically decreased radial strength at the ends of braided stents by configuring the end portion as a wound architecture.

Stents having one or more elevations of greater diameter than the rest of the stent structure have also been proposed as having a number of benefits, including having increased radial strength in the elevations. Such designs are particularly known with respect to braided stent architectures. U.S. Pat. No. 5,575,818 to Pinchuk, U.S. Pat. No. 5,725,547 to Chuter, and U.S. Pat. No. 5,993,483 to Gianotti, all incorporated herein by reference, discuss braided stents having such elevations.

There is still a need in the art, however, for additional methods for fabricating braided stents with elevations, as well as a need for braided stent structures that incorporate elevations and other radial-strength-increasing attributes in their design to minimize endoleaks.

SUMMARY OF THE INVENTION

One aspect of the invention comprises a braided modular stent comprising a first component and a second component, each component comprising an hourglass-shaped interface. Each hourglass shaped interface comprises a reduced diameter section positioned between two sloped sections, each sloped section extending between the reduced diameter section and one of a plurality of nominal diameter sections, the reduced diameter section having a greater radial strength than the nominal diameter sections. The reduced diameter section of the hourglass-shaped interface may have a greater braiding angle than the nominal diameter sections, may have different metallurgical properties than the nominal diameter sections, and/or may comprise filaments having a greater cross-sectional area than the filaments in the nominal diameter sections. In one embodiment, the first component comprises a body having at least one integral leg stump depending therefrom, each leg stump comprising an hourglass-shaped interface, and the second component comprises a leg adapted to interface with the leg stump. At least one of the first component or the second component may have an end section with a wound architecture, such as a hexagonal cell architecture. The stent may also comprise one or more circumferential elevations, such as one in which the circumferential elevation is maintained by a plurality of sutures affixed between the second section and the third section.

At least one of the first component or the second component may comprise a sealing region for providing an endoleak-resistant seal between the stent and a body lumen into which the stent is adapted to be installed. The sealing region has a greater radial strength than portions of the stent adjacent to the sealing region. The greater radial strength in the sealing region may comprise one of more of: (a) a first braiding angle greater than a second braiding angle in the portions of the stent adjacent to the sealing region; (b) a first set of metallurgical properties different than a second set of metallurgical properties in the portions of the stent adjacent to the sealing region; (c) first regions of braided filaments in which the filaments have a first cross-sectional area that is greater a second cross-sectional area in second regions of braided filaments in the portions of the stent adjacent to the sealing region; and (d) a first diameter greater than a second diameter in the portions of the stent adjacent to the sealing region. The sealing region may have a ringlike geometry or a spherical geometry.

In one embodiment, the invention comprises a braided modular stent comprising: a body, two legs, and a plurality of hourglass-shaped interfaces, one on each leg stump and one on each leg, for interlocking the legs to the leg stumps. The body has two integral leg stumps depending therefrom, an end section having a hexagonal cell wound architecture opposite the leg stumps, and a sealing region adjacent the end section. The sealing region has a greater radial strength than a portion of the stent adjacent to the sealing region and provides an endoleak-resistant seal between the stent and a body lumen into which the stent is adapted to be installed. Each hourglass shaped interface comprises a reduced diameter section positioned between two sloped sections, each sloped section extending between the reduced diameter section and one of a plurality of nominal diameter sections, the reduced diameter section having a greater braiding angle than the nominal diameter sections. The sealing region may comprise one or more of the aspects described above with respect to braiding angle, metallurgical properties, cross-sectional area, and greater diameter.

Another aspect of the invention comprises a method for fabricating a braided stent comprising at least one circumferential elevation. The elevation comprises a first section of the stent having a first outer diameter that is greater than a second outer diameter of a second section of the stent distally adjacent the elevation and a third section of the stent proximally adjacent the elevation. The method comprises the steps of braiding one or more filaments together to create the braided stent in a first configuration in which the second section and the third section are a first distance apart. Then, at least a portion of the braided stent is placed on a mandrel having essentially the second diameter. The second section is next repositioned axially closer to the third section in an axially compressed configuration, causing the first section between the second section and the third section to bulge radially outward into the circumferential elevation. The mandrel and the stent are then heat treated with the stent in the axially compressed configuration to permanently set the circumferential elevation.

A further aspect of this invention comprises another method for fabricating a braided stent comprising at least one circumferential elevation comprising a first section of the stent having a first outer diameter that is greater than a second outer diameter of a second section of the stent distally adjacent the elevation and a third section of the stent proximally adjacent the elevation. This method comprises the steps of braiding one or more filaments together to create the braided stent having a plurality of overlapping filaments and a tubular shape with an interior. The braided stent has a first configuration in which the plurality of filaments includes a plurality of first overlaps in the second section positioned a first axial distance apart from a plurality of corresponding axially-aligned second overlaps in the third section. From the interior of the braided tubular stent, each of a plurality of the first overlaps is attached to its corresponding axially-aligned second overlap axially using a suture with a length less than the first distance, so that the first section between the second section and the third section bulges radially outward to form the circumferential elevation.

Yet another aspect of the invention comprises a method for fabricating a braided stent comprising at least one circumferential elevation, comprising the steps of braiding a plurality of filaments together to create the braided stent; positioning an annealing mass inside of the braided stent, and heat treating the stent with the annealing mass positioned inside to permanent set the circumferential elevation. The annealing mass comprises a geometry sufficient to produce the circumferential elevation, such as a spherical or truncated spherical geometry, a cylindrical or ringlike geometry, or a partial mandrel geometry, but has a length less than the length of the stent.

Any of the methods of this invention may be particularly advantageous for providing the circumferential elevation on the stent in a customized location corresponding to a specific lumen geometry of a patient into which the stent is to be implanted.

DETAILED DESCRIPTION OF INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 1A:
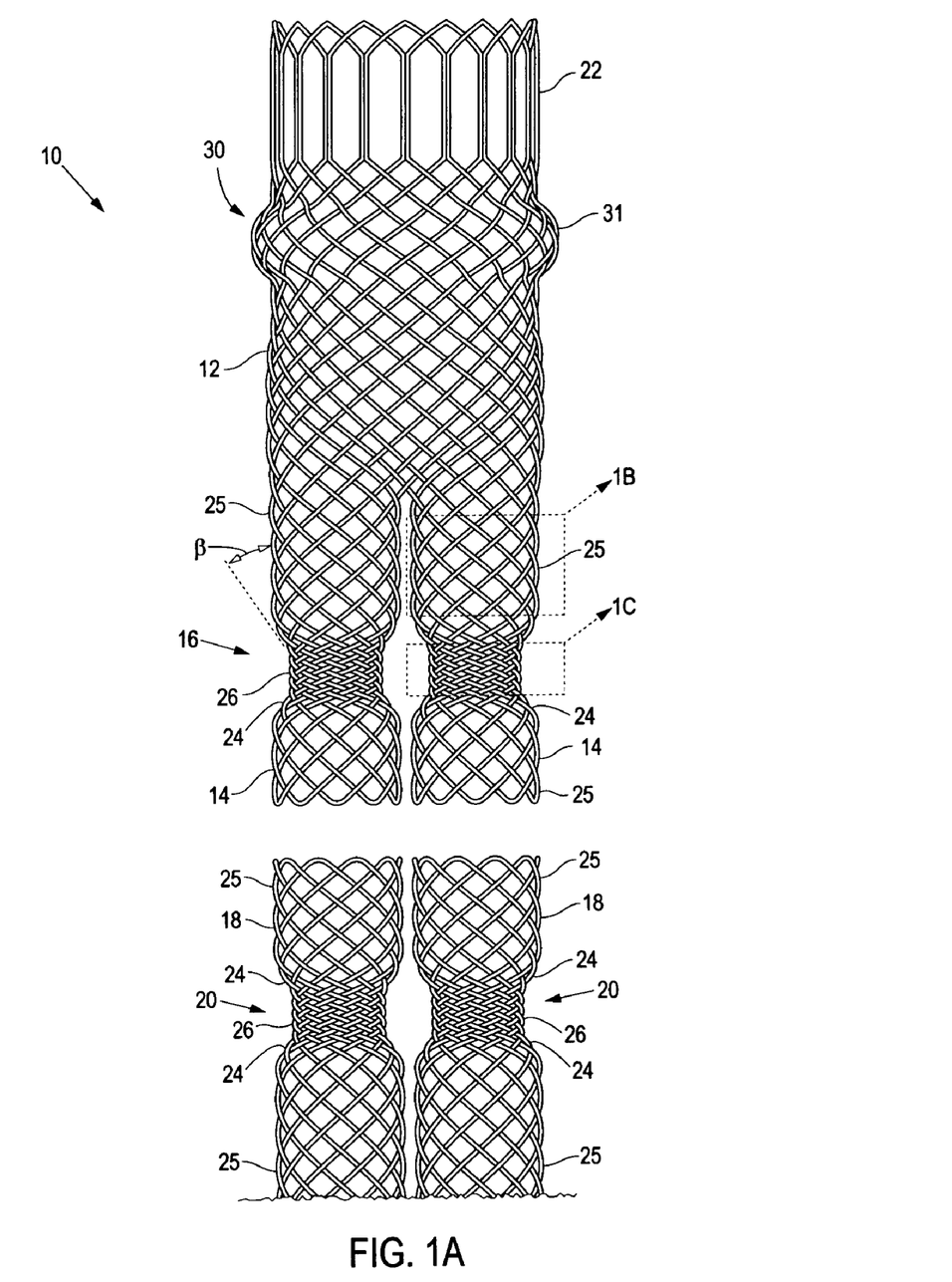
FIG. 1A is a plan view illustration of an exemplary stent embodiment of this invention having hourglass-shaped interfaces and a sealing region comprising a circumferential elevation.
Figure 1B:
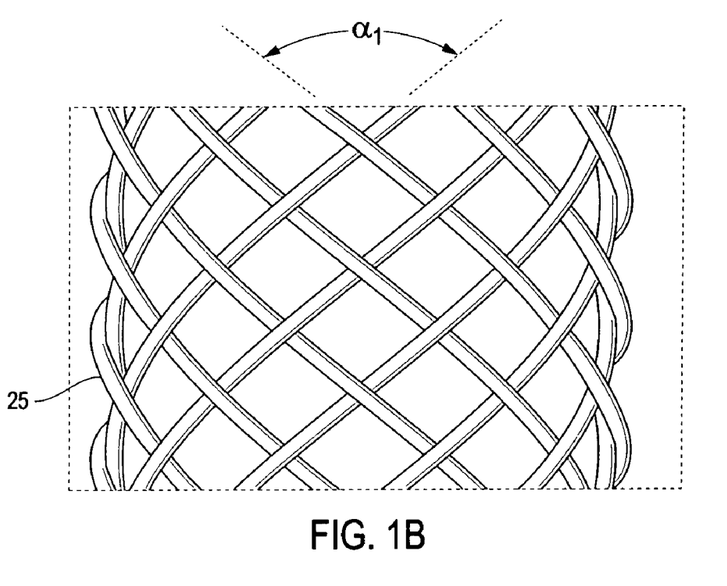
FIG. 1B is a magnified plan view illustration of a nominal portion of the stent of FIG. 1A.
Figure 1C:
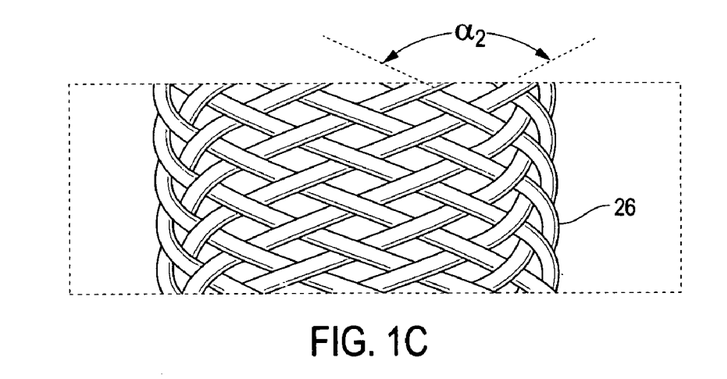
FIG. 1C is a magnified plan view illustration of a reduced diameter portion of an hourglass-shaped interface in the stent of FIG. 1A.

Referring now to FIGS. 1A–1C, there is shown a modular bifurcated stent 10 of the present invention. The stent comprises three modular sections: a body 12 having two leg stumps 14 having first hourglass-shaped interfaces 16, and a pair of legs 18, each having a second hourglass-shaped interface 20 adapted to interlock with one of the first interfaces. Body 12 further comprises a wound end section 22 having a hexagonal cell architecture. End section 22 may comprise any form of wound architecture, as described in U.S. patent application Ser. No. 09/442,165, filed Nov. 16, 1999, by Chouinard et al., assigned to the common assignee of this invention, and incorporated herein by reference. Only the distal end of legs 18 are shown in FIG. 1A, but the proximal ends may also have a wound architecture, such as a hexagonal cell architecture. The architecture of the distal end of the body and proximal ends of the legs are not limited to any particular architecture, however, and may be braided or wound.

Each of the hourglass-shaped interfaces 16 and 20 comprise a pair of sloped portions 24 and a reduced diameter portion 26 located between the sloped diameter portions. Each sloped diameter portion extends between the reduced diameter portion 26 and one of two nominal diameter portions 25. The nominal diameter portions 25 have a braid angle $\alpha_1$, as shown in the magnification provided as FIG. 1B, which is the same as in the remaining portions of the stent. The reduced diameter portion 26 has an increased braid angle $\alpha_2$ that is greater than the braid angle in the remaining portions of the stent, as shown in the magnification provided as FIG. 1C. The sloped portions may have a braid angle of $\alpha_1$ and $\alpha_2$, or may comprise a gradient braid angle ranging between $\alpha_1$ and $\alpha_2$. The increased braid angle provides an increased radial strength in the reduced diameter portion. Thus, the combination of the hourglass configuration and the increased radial strength in the interlocking regions provides a more secure fit than interlocking regions lacking either or both of these characteristics. The secureness of the fit between interlocking regions is also dependent upon slope $\beta$ of sloped portions 24. Although this slope must be greater than 0, the invention is not limited to any particular slope.

Other methods of increasing the radial strength in the reduced diameter section may also be used in addition to or instead of the increased braiding angle. For example, as described in U.S. patent application Ser. No. 09/442,192, filed Nov. 16, 1999, by Zarbatany et al., assigned to the common assignee of this invention, and incorporated by reference, the reduced diameter region may have a first set of metallurgical properties different than a second set of metallurgical properties in the remaining portions of the stent. For example, the differing metallurgical properties may arise from the different regions having different annealing histories, as disclosed by Zarbatany. The greater radial strength may also be provided by using a filament having a greater cross-sectional area in the reduced diameter section of the hourglass-shaped interface, as also generally discussed by Zarbatany.

Each of the modular elements of the stent have a radially-compressed configuration for introducing the stent into the body through the body lumen, such as in a sheath as is known in the art. Each element also has a non-radially-compressed configuration for deployment in the lumen. Typically, the body 12 is deployed in the body lumen first, followed each of the legs 18. When deployed in this sequence, hourglass-shaped interfaces 16 on body 12 are the outermost interfacing members and interfaces 20 on legs 18 are the innermost interfacing members. If the sequence is reversed, however, interfaces 20 may be the outermost interfacing members and interfaces 16 may be the innermost interfacing members. The reduced diameter portions 26 of the innermost interfacing members may be equal to or slightly larger than the reduced diameter portions 26 of the outer interfacing members in their respective non-radially compressed configurations. The equal or slightly different diameters creates an opposition of compressive and expansive forces between the interlocking members that holds the modular components together. In particular, because the reduced diameter sections also have increased radial strengths as compared to the rest of the device, the opposing forces are greater than if the reduced diameter sections merely had the same radial strength as the rest of the stent.

Braided bifurcated devices are known in the art, for example as described in U.S. patent application Ser. No. 09/494,704, filed Jan. 31, 2000, by Chouinard et al., assigned to the assignee of the present invention, and incorporated herein by reference. To make the device shown in FIG. 1A, body 12 and legs 18 may may first be fabricated by any process known in the art. In particular, body 12 may be fabricated by the process detailed in the '704 application, except that the portions of the mandrel corresponding to the leg stumps 14 are fabricated with an hourglass shape corresponding to the hourglass shape desired for portions 16 of the stent, as described herein.

When braiding the reduced diameter portions 26 of the hourglass-shaped interface, the relationship between the mandrel and the braiding machine may be changed to provide a greater braiding angle to provide increased radial strength. Where the radial strength in the reduced diameter section is further enhanced or provided by a greater filament cross-section as compared to the filament cross-section in other portions of the stent, tapered filaments having the desired cross-sectional area in the regions used for making the reduced diameter section may be used. The use of tapered filaments in braided stents is discussed generally in U.S. patent application Ser. No. 09/494,980, filed Jan. 31, 2000, by Chouinard et al., assigned to the assignee of the present invention, and incorporated herein by reference. The braiding process for hourglass-shaped interfaces 20 of legs 18 is similar to the process used for interfaces 22.

A stent such as is shown in FIG. 1A may also have additional features, such as sealing region 30 and/or a circumferential elevation 31. As shown in FIG. 1A, sealing region 30 comprises a circumferential elevation 31, but the sealing region may comprise other means for increasing the seal between the stent and a body lumen, as discussed herein later. Although the sealing region is shown adjacent the distal end of body 12 of stent 10, sealing regions may also or instead be provided at the proximal ends of legs 18, or anywhere along the length of the stent. Furthermore, although circumferential elevation 31 is shown in FIG. 1A as comprising a sealing region, circumferential elevations have also surprisingly been found to improve the articulation of the device at the elevation. Accordingly, circumferential elevations 31 may be usefully positioned anywhere along the length of a stent where it is desired to improve articulation, not only where it is desired to prevent endoleaks. Thus, for example, where it is known that a certain portion of a stent may be subjected to bending because of the tortuousity of the lumen into which it is implanted, circumferential elevation 31 may be formed in a specific location tailored to the geometry of the lumen. The methods previously described in the art, using stepped mandrels or tubes for forming protrusions are not optimal for fabrication of circumferential elevations in customized locations. The method of the present invention provides a method for forming a circumferential elevation in any location on a device, without need for a specially constructed mandrel.

Figure 2A:
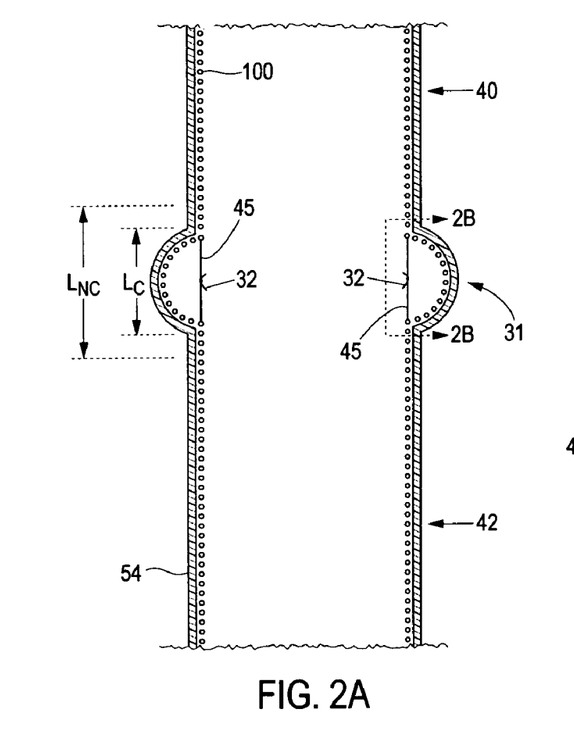
FIG. 2A is a cross-sectional illustration of a portion of a stent having a circumferential elevation held in place by sutures.
Figure 2B:
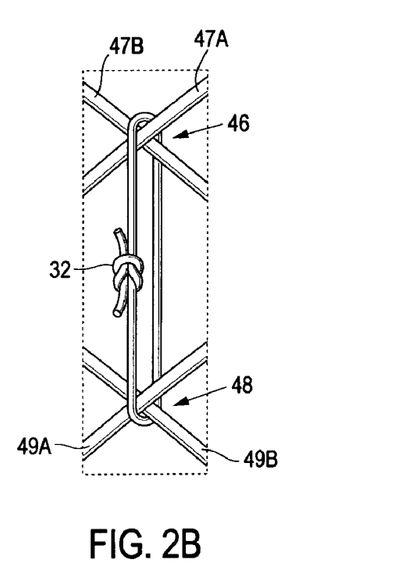
FIG. 2B is a plan view illustration of a magnified portion of the stent of FIG. 2A, showing sutures wrapped around overlaps of the braided filaments.

In a first method, illustrated in FIGS. 2A and 2B, elevation 31 on stent 100 is formed by connecting a plurality of sutures 45 between overlaps in the first portion 40 of the stent with overlaps in the second portion 42 of the stent. For example, as shown in FIG. 2B, a first overlap 46, formed by overlapping filaments 47A and 47B, may be connected to a second overlap 48, formed by overlapping filaments 49A and 49B. Each suture 45 has a length $L_C$ that is less than the length $L_{NC}$ between overlaps 46 and 48 in a non-axially-compressed configuration. Any number of sutures may be used, ranging from at least three to as many sutures as there are overlaps to which to attach. Any type of filamentary attachment may be used to connect overlaps 46 and 48, such as staples, cables, or wire such as is used for braiding the stent.

Because the sutures must be located on the inside of tubular stent 100, as shown in FIG. 2A, so that the sutures do not restrict the radial outward protrusion of the circumferential elevation, a suturing device such as a CAPIO® device manufactured by Boston Scientific of Boston, Mass. may be used. Such devices are described generally in U.S. patent application Ser. No. 5,540,704 and related patents to Gordon et al., incorporated herein by reference. To fabricate the circumferential elevation, the stent 100 is first fabricated by any of the methods known in the art, and then the suturing device is threaded inside the lumen of the stent. The device is actuated to thread the suture around a first overlap 46, then the needle is reloaded and the device positioned and actuated to thread the suture around a second overlap 48. The suture is then drawn to a desired amount of tightness and a knot 32 is tied to fix the suture with length $L_C$. Other sutures are then fabricated in positions circumferentially offset from the first suture. The above description provides only one exemplary method of making the sutures inside the lumen, but the invention is not limited to any particular method, so other methods may also be used.

Figure 3:
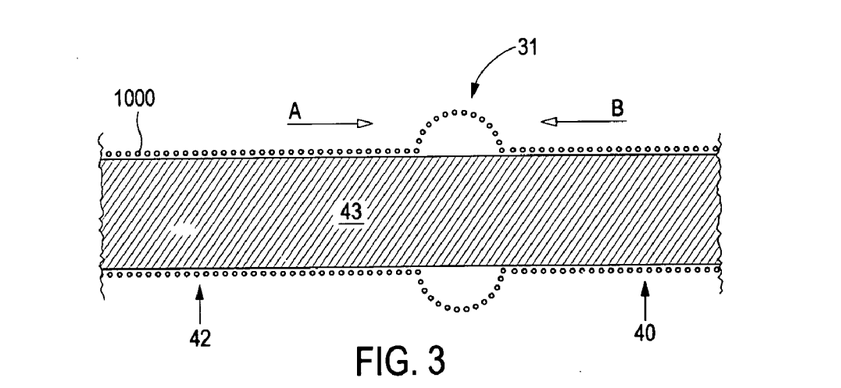
FIG. 3 is a cross-sectional illustration of an intermediate step in an exemplary fabrication process on a mandrel of a stent having a circumferential elevation.

Referring now to FIG. 3, the inventors have also found that mounting non-radially-compressed braided stent 1000 on mandrel 43 and pushing adjacent portions 40 and 42 of the stent together toward one another along arrows A and B into an axially compressed configuration forms circumferential elevation 31. Elevation 31 can then be fixed in place by temporarily holding stent portions 40 and 42 in their axially compressed configuration, such as with straps or clamps (not shown) that frictionally hold the stent to the mandrel, while the stent is heat-treated. For example, a standard hose clamp well-known in the art may be sufficient for holding the stent on the mandrel, but the method is not limited to any particular clamp or strap structure.

Although elevation 31 is shown as part of stent 10 in FIG. 1A, stents having a similar elevation may have none, any, or all of the other features of stent 10. For example, a braided stent having an elevation 31 as described herein may not necessarily be bifurcated, modular, or have a wound end section, but may have any combination of these features. For that matter, although stent 10 is shown as being bifurcated, the stent is not limited to stents adapted for implantation in bifurcated lumen, but rather may have more than two branches, or no branches at all. Furthermore, although sealing region 30 for minimizing endoleaks as shown in FIG. 1A comprises circumferential elevation 31, sealing regions in accordance with this invention are not limited to circumferential elevations.

Sealing regions of a stent that provide increased endoleak resistance may comprise any means of increasing the radial strength of a region of the stent, including a combination of multiple means. Thus, the sealing region may comprise one or more of a circumferential elevation, an increased braiding angle, an increased filament cross-sectional area, and different metallurgical properties as compared to regions distally and proximally adjacent the sealing region. In fact, a sealing ring comprising both a circumferential elevation 31 and an increased braiding angle, such as shown in FIG. 1C, is particularly advantageous. The combination of circumferential elevation and increased braiding angle is also particularly advantageous for providing articulation. The sealing region may comprise a structure created by the methods described herein, or may comprise any structure created by any method known in the art for creating an enhanced seal. The sealing region may be integral to the filamentary architecture, or may comprise an outer balloon or collars placed on the outside diameter of the stent, as described in but not limited to U.S. Pat. Nos. 5,665,117 and 5,843,160 to Rhodes, and No. U.S. Pat. No. 5,693,088 to Lazarus, all incorporated herein by reference. An eversion of the stent, as described in U.S. Pat. No. 5,709,713 to Evans et al., also incorporated herein by reference, may also be used in the sealing region.

Figure 4:
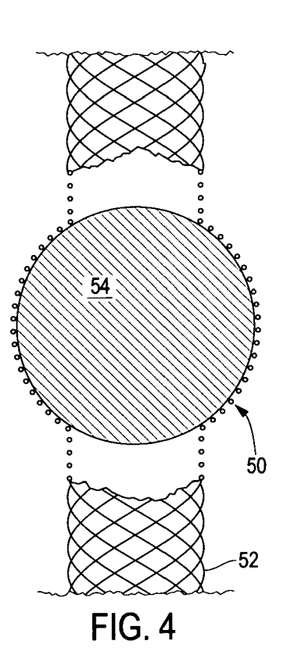
FIG. 4 is a partial cross sectional illustration of a stent having a sealing region with a spherical geometry undergoing an annealing step.
Figure 5A:
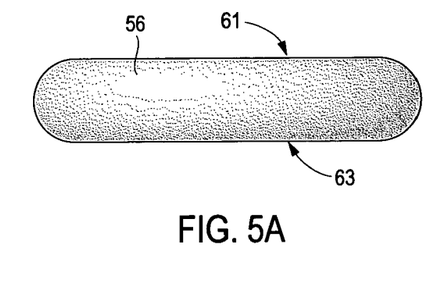
FIG. 5A is a perspective view of an annealing mass having a cylindrical shape.
Figure 5B:
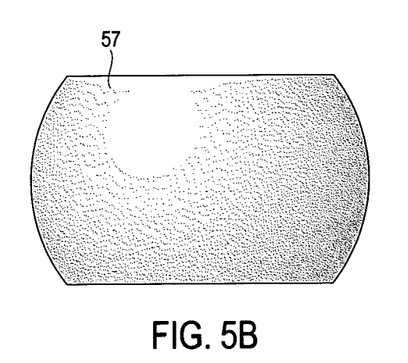
FIG. 5B is a perspective view of an annealing mass having a truncated spherical shape.
Figure 5C:
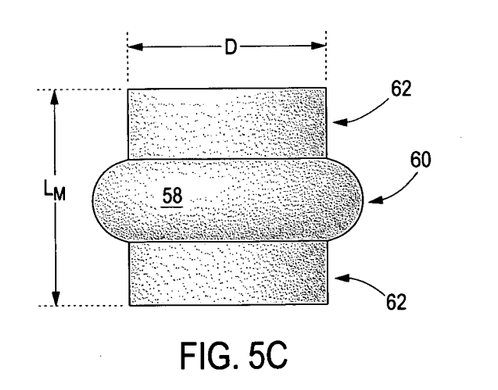
FIG. 5C is a perspective view of an annealing mass having a partial mandrel shape.

The shape of the circumferential elevation for use as a sealing region or articulation joint may be ringlike as shown in FIGS. 1A–3, or spherical, as shown in FIG. 4. FIG. 4 shows stent 52 being annealed on an annealing mass 54 having a spherical geometry for creating spherical sealing region 50. In the exemplary embodiment, annealing mass 54 is placed inside the stent at the desired location, leaving the rest of the stent unsupported during the annealing step. Similarly, as shown in FIGS. 5A–5C, annealing masses may be in the shape of cylinders 56, truncated spheres 57, partial mandrels 58, or masses of any geometry known in the art. Cylinder 56 may be solid across its cross-section, or may have a hollow center, like a ring. The term "cylinder" as used herein is not limited to right cylinders, but also includes shapes such as shown in FIG. 5A, where the lateral periphery of the mass is curved from end 61 to end 63. Spherical sealing region 50 or other such regions may also be formed by heat treatment of stent 52 on a contoured mandrel (not shown) extending for the full length of the stent and having the desired contour to form the sealing region, as is known in the art.

The advantage of the annealing masses 50, 56, 57, and 58 is that they may be placed inside of a stent in a desired location for creating a sealing region or articulation joints, thereby allowing manufacture of such regions or joints in customized locations without requiring entire customized mandrels to be made. Mandrel portion 58 comprises a protruding region 60 surrounded by non-protruding regions 62 and having an overall length $L_M$ shorter than the length of the stent to be formed with the annealing mass. In one embodiment, length $L_M$ may be less than or equal to the nominal diameter D of the portion of the stent in which the annealed mass is adapted to be placed to form the circumferential elevation. Non-protruding regions 62 may have a constant diameter approximately equal to the corresponding stent diameter, of may be tapered or otherwise shaped for easy insertion and removal from the stent. Although sealing regions with exemplary ringlike and spherical geometries are shown herein, the sealing region and the annealing masses used to create such sealing regions are not limited to any particular geometry.

The finished stent, in particular stents used for treating aneurysms, may be covered with an attached graft 54, as shown in FIG. 2A. The graft may be an outer covering, an inner lining, or a combination thereof. For the embodiment shown in FIG. 2A using sutures to affix the circumferential elevation, the graft comprises an outer covering so as not to interfere with the sutures. The graft is also typically attached after the sutures are installed, to avoid puncturing the graft during fabrication of the circumferential elevation. Similarly, in heat-treated embodiments, the graft is typically attached after the heat-treatment has been completed.

While the present invention has been described with respect to specific embodiments thereof, it is not limited thereto. Therefore, the claims that follow are intended to be construed to encompass not only the specific embodiments described but also all modifications and variants thereof which embody the essential teaching thereof.

What is claimed:

1. A braided modular stent comprising a first component and a second component, each component comprising an hourglass-shaped interface, each hourglass shaped interface comprising a reduced diameter section positioned between two sloped sections, each sloped section extending between the reduced diameter section and one of a plurality of nominal diameter sections, the reduced diameter section having a greater radial strength than the nominal diameter sections, wherein reduced diameter section of the hourglass-shaped interface has a greater braiding angle than the nominal diameter sections.

2. A braided modular stent comprising a first component and a second component, each component comprising an hourglass-shaped interface, each hourglass shaped interface comprising a reduced diameter section positioned between two sloped sections, each sloped section extending between the reduced diameter section and one of a plurality of nominal diameter sections, the reduced diameter section having a greater radial strength than the nominal diameter sections, wherein the reduced diameter section of the hourglass-shaped interface comprises filaments having a first set of metallurgical properties different than a second set of metallurgical properties in the nominal diameter sections.

3. A braided modular stent comprising a first component and a second component, each component comprising an hourglass-shaped interface, each hourglass shaped interface comprising a reduced diameter section positioned between two sloped sections, each sloped section extending between the reduced diameter section and one of a plurality of nominal diameter sections, the reduced diameter section having a greater than radial strength than the nominal diameter sections, wherein the reduced diameter section of the hourglass-shaped interface comprises a plurality of first regions of braided filaments in which the filaments have a first cross-sectional area that is, greater than a second cross-sectional area in a plurality of second regions of braided filaments in the nominal diameter sections.

4. A braided modular stent comprising a first component and a second component, each component comprising an hourglass-shaped interface, each hourglass shaped interface comprising a reduced diameter section positioned between two sloped sections, each sloped section extending between the reduced diameter section and one of a plurality of nominal diameter sections, the reduced diameter section having a greater radial strength than the nominal diameter sections, wherein at least one of the first component or the second component has an end section having a non-braided wound architecture.

5. The stent of claim 4, wherein the non-braided wound architecture comprises a hexagonal cell architecture.

6. A braided modular stent comprising a first component and a second component, each component comprising an hourglass-shaped interface, each hourglass shaped interface comprising a reduced diameter section positioned between two sloped sections, each sloped section extending between the reduced diameter section and one of a plurality of nominal diameter sections, the reduced diameter section having a greater radial strength than the nominal diameter sections, further comprising one or more circumferential elevations, each elevation comprising a first section of the stent having a first diameter that is greater than a second diameter of a second section of the stent distally adjacent the elevation and a third diameter of a third section of the stent proximally adjacent the elevation.

7. The stent of claim 6, wherein the one or more circumferential elevations is maintained by a plurality of filaments affixed between the second section and the third section.

8. The stent of claim 7, wherein each filament connects a first overlap of braided filaments in the first portion to a corresponding second overlap in the second portion.

9. The stent of claim 8, wherein the filament comprises a suture, a staple, or a length of wire.

10. A braided modular stent comprising a first component and a second component, each component comprising an hourglass-shaped interface, each hourglass shaped interface comprising a reduced diameter section positioned between two sloped sections, each sloped section extending between the reduced diameter section and one of a plurality of nominal diameter sections, the reduced diameter section having a greater radial strength than the nominal diameter sections, wherein at least one of the first component or the second component further comprises a sealing region for providing an endoleak-resistant seal between the stent and a body lumen into which the stent is adapted to be installed and the sealing region comprises a greater radial strength than portions of the stent adjacent to the sealing region.

11. The stent of claim 10, wherein the sealing region has a first braiding angle greater than a second braiding angle in the portions of the stent adjacent to the sealing region.

12. The stent of claim 10, wherein the sealing region has a first set of metallurgical properties different than a second set of metallurgical properties in the portions of the stent adjacent to the sealing region.

13. The stent of claim 12, wherein the first set of metallurgical properties are caused by a first annealing history and the second set of metallurgical properties are caused by a second annealing history.

14. The stent of claim 10 comprising a plurality of braided filaments, wherein the sealing region comprises first regions of the braided filaments in which the filaments have a first cross-sectional area that is greater a second cross-sectional area in second regions of the braided filaments in the portions of the stent adjacent to the sealing region.

15. The stent of claim 10, wherein the sealing region has a first diameter greater than a second diameter in the portions of the stent adjacent to the sealing region.

16. The stent of claim 15, wherein the first diameter in the sealing ring is maintained by a plurality of filaments affixed between portions of the stent adjacent to the sealing region that hold the adjacent portions in an axially compressed configuration with respect to one another.

17. A braided modular stent comprising a first component and a second component, each component comprising an hourglass-shaped interface, each hourglass shaped interface comprising a reduced diameter section positioned between two sloped sections, each sloped section extending between the reduced diameter section and one of a plurality of nominal diameter sections, the reduced diameter section having a greater radial strength than the nominal diameter sections, wherein the sloped sections have a radial strength greater than the nominal diameter sections.

18. The stent of claim 17, wherein the first component comprises a body having at least one integral leg stump depending therefrom, each leg stump comprising an hourglass-shaped interface, and the second component comprises a leg adapted to interface with the leg stump.

19. The stent of claim 18 comprising two integral leg stumps and two legs, each leg adapted to interface with one of the leg stumps.

20. The stent of claim 17, wherein at least one of the first component or the second component further comprises a sealing region for providing an endoleak-resistant seal between the stent and a body lumen into which the stent is adapted to be installed.

21. The stent of claim 20, wherein the sealing region has a ringlike geometry.

22. The stent of claim 17, wherein the first component and the second component each further comprise a graft covering, lining, or combination thereof.

23. A braided modular stent comprising a first component and a second component, each component comprising an hourglass-shaped interface, each hourglass shaped interface comprising a reduced diameter section positioned between two sloped sections, each sloped section extending between the reduced diameter section and one of a plurality of nominal diameter sections, the reduced diameter section having a greater radial strength than the nominal diameter sections, at least one of the first component or the second component comprising a sealing region for providing an endoleak-resistant seal between the stent and a body lumen into which the stent is adapted to be installed, the sealing region having a spherical geometry.

24. A braided modular stent comprising a first component and a second component, each component comprising an hourglass-shaped interface, each hourglass shaped interface comprising a reduced diameter section positioned between two sloped sections, each sloped section extending between the reduced diameter section and one of a plurality of nominal diameter sections, the reduced diameter section having a greater radial strength than the nominal diameter sections, wherein the sloped sections have a radial strength less than or equal to the nominal diameter sections.

25. The stent of claim 24, wherein the first component comprises a body having at least one integral leg stump depending therefrom, each leg stump comprising an hourglass-shaped interface, and the second component comprises a leg adapted to interface with the leg stump.

26. The stent of claim 25 comprising two integral leg stumps and two legs, each leg adapted to interface with one of the leg stumps.

27. The stent of claim 24, wherein at least one of the first component or the second component further comprises a sealing region for providing an endoleak-resistant seal between the stent and a body lumen into which the stent is adapted to be installed.

28. The stent of claim 27, wherein the sealing region has a ringlike geometry.

29. The stent of claim 24, wherein the first component and the second component each further comprise a graft covering, lining, or combination thereof.

30. A braided modular stent comprising:
   a body having two integral leg stumps depending therefrom, an end section having a hexagonal cell wound architecture opposite the leg stumps, and a sealing ring adjacent the end section for providing an endoleak-resistant seal between the stent and a body lumen into which the stent is adapted to be installed, the sealing region having a greater radial strength than a portion of the stent adjacent to the sealing region; and
   two legs, wherein each of said stumps and each of said legs has an hourglass-shaped interface for interlocking the legs to the leg stumps, each hourglass shaped interface comprising a reduced diameter section positioned between two sloped sections, each sloped section extending between the reduced diameter section and one of a plurality of nominal diameter sections, the reduced diameter section having a greater radial strength than the nominal diameter sections.

31. The braided modular stent of claim 30 wherein the sealing region comprises one or more of:
   (a) a first braiding angle greater than a second braiding angle in the portions of the stent adjacent to the sealing region;
   (b) a first set of metallurgical properties different than a second set of metallurgical properties in the portions of the stent adjacent to the sealing region;
   (c) a plurality of first regions of braided filaments in which the filaments have a first cross-sectional area that is greater a second cross-sectional area in a plurality of second regions of braided filaments in the portions of the stent adjacent to the sealing region; and
   (d) a first diameter greater than a second diameter in the portions of the stent adjacent to the sealing region.

32. The braided modular stent of claim 30 wherein the reduced diameter section of the hourglass-shaped interface comprises one or more of:
   (a) a first braiding angle greater than a second braiding angle in the nominal diameter sections;
   (b) a first set of metallurgical properties different than a second set of metallurgical properties in the nominal diameter sections; and
   (c) a plurality of first regions of braided filaments in which the filaments have a first cross-sectional area that is greater a second cross-sectional area in a plurality of second regions of braided filaments in the nominal diameter sections.

33. The stent of claim 30 wherein the body and the legs each further comprise a graft covering or lining.

* * * * *